US009119870B2

(12) United States Patent
Arad et al.

(10) Patent No.: US 9,119,870 B2
(45) Date of Patent: Sep. 1, 2015

(54) VISCOSUPPLEMENTATION WITH ALGAL POLYSACCHARIDES IN THE TREATMENT OF ARTHRITIS

(75) Inventors: Shosh Arad, Omer (IL); Dan Atar, Omer (IL)

(73) Assignee: Ben Gurion University of the Negev Research and Development Authority, Beer Sheva (IL)

( * ) Notice: Subject to any disclaimer, the term of this patent is extended or adjusted under 35 U.S.C. 154(b) by 1076 days.

(21) Appl. No.: 12/096,290

(22) PCT Filed: Dec. 7, 2006

(86) PCT No.: PCT/IL2006/001412
§ 371 (c)(1),
(2), (4) Date: Sep. 18, 2008

(87) PCT Pub. No.: WO2007/066340
PCT Pub. Date: Jun. 14, 2007

(65) Prior Publication Data
US 2009/0017058 A1      Jan. 15, 2009

(30) Foreign Application Priority Data

Dec. 8, 2005    (IL) .......................................... 172477

(51) Int. Cl.
| | |
|---|---|
| *A61K 36/00* | (2006.01) |
| *A61K 36/04* | (2006.01) |
| *A61K 31/715* | (2006.01) |
| *A61K 31/737* | (2006.01) |
| *A61K 36/02* | (2006.01) |

(52) U.S. Cl.
CPC ............. *A61K 31/715* (2013.01); *A61K 31/737* (2013.01); *A61K 36/02* (2013.01)

(58) Field of Classification Search
CPC ...................................................... A61K 36/04
USPC ............................................ 424/725, 195.17
See application file for complete search history.

(56) References Cited

U.S. PATENT DOCUMENTS

| | | | | |
|---|---|---|---|---|
| 4,281,061 A | * | 7/1981 | Zuk et al. ........................ | 435/7.9 |
| 5,612,321 A | * | 3/1997 | Nguyen ........................... | 514/54 |
| 5,910,512 A | * | 6/1999 | Conant ........................... | 514/617 |
| 2005/0196410 A1 | | 9/2005 | Daniels | |

FOREIGN PATENT DOCUMENTS

| | | | |
|---|---|---|---|
| CA | 2249103 | | 4/1999 |
| FR | 2785909 A1 | * | 5/2000 |
| JP | 11228437 A | * | 8/1999 |
| WO | WO 01/82936 A1 | | 11/2001 |

OTHER PUBLICATIONS

Arad et al. "Antiviral activity of sulfated polysaccharides of marine red algae." *Recent Advances in Marine Biotechnology: Biomaterials from Aquatic and Terrestrial Organisms*. Science Publishers Inc., Enfield, NH, USA (2006), pp. 37-62.
Arad et al. "Superior Biolubricant from a Species of Red Microalga." *Langmuir: The ACS Journal of Surfaces and Colloids*. Aug. 15, 2006, vol. 22, No. 17, pp. 7313-7317.
Dubois et al. "Colormetric Method for Determination of Sugars and Related Substances." *Analytical Chemistry*. vol. 28, No. 3, Mar. 1956, pp. 350-356.
Fraser et al. "The Kinetics of Hyaluronan in Normal and Acutely Inflamed Synovial Joints: Observations With Experimental Arthritis in Sheep." *Seminars in Arthritis and Rheumatism*. vol. 22, No. 6, Suppl1 (June), 1993, pp. 9-17.
George. "Intra-articular hyaluronan treatment for osteoarthritis." *Annals of the Rehumatic Diseases*. 1998, vol. 57, pp. 637-640.
Geresh et al. "The Extracellular Polysaccharides of the Red Microalgae: Chemistry and Rheology." *Bioresource Technology*. vol. 38, 1991, pp. 195-201.
Geresh et al. "Structure of 3-*O*—(x-D-glucopyranosyluronic acid)-L-galactopyranose, an aldobiouronic acid isolated from the polysaccharides of various unicellular red algae." *Carbohydrate Research*. vol. 208, 1990, pp. 301-305.
Gourdon et al. "Lubrication by the red microalgae *Porphyridium* sp. Polysaccharide." American Physical Society, APS March Meeting, Mar. 22-26, 2004. Palais des Congres Montreal, Quebec, Canada.
Gourdon et al. "Superlubricity of a natural polysaccharide from the alga *Porphyridium* sp." American Physical Society, APS March Meeting, Mar. 21-25, 2005. Los Angeles, CA.
Hansra et al. "Carrageenan-induced arthritis in the rat." *Inflammation*. vol. 24, No. 2, 2000, pp. 144-155.
Henderson et al. "Intra-articular injections of 750 kD hyaluronan in the treatment of osteoarthritis: a randomized single centre double-blind placebo-controlled trial of 91 patients demonstrating a lack of efficacy." *Annals of the Rheumatic Diseases*. vol. 53, 1993, pp. 529-534.

(Continued)

*Primary Examiner* — Chris R Tate
*Assistant Examiner* — Deborah Davis
(74) *Attorney, Agent, or Firm* — Merchant & Gould P.C.

(57) ABSTRACT

A joint-lubricating composition for treating degenerative joint disorders is provided, having microalgal polysaccharides in an aqueous solution, wherein the polysaccharides are stable and non-immunogenic. Further provided is a method for treating a joint disorder by injecting into the joint a viscous aqueous solution of a polysaccharide, wherein the disorder is, for example, arthritis, and the polysaccharide originates, for example, from a red alga.

5 Claims, No Drawings

(56) References Cited

OTHER PUBLICATIONS

Huheihel et al. "Activity of *Porphyridium* sp. Polysaccharide against herpes simplex viruses in vitro and in vivo." *Journal of biochemical and biophysical methods*. vol. 50, No. 2-3, 2002, pp. 189-200.

Lupescu et al. "Structure of some sulfated sugars isolated after acid hydrolysis of the extracellular polysaccharide of *Porphyridium* sp., a unicellular red alga." *Carbohydrate Research*. vol. 210, 1991. pp. 349-352.

Matsui et al. "Sulfated Polysaccharides from Red Microalgae Have Antiinflammatory Properties in Vitro and In Vivo." *Applied Biochemistry and Biotechnology*. vol. 104, No. 1, Jan. 2003, pp. 13-22.

Roman et al. "Intra-articular Treatment with Hyaluronic Acid. Comparative Study of Hyalgan and Adant." *Clinical Rheumatology*. vol. 19, No. 3, 2000, pp. 204-206.

Tannin-Spitz et al. "Antioxidant activity of the polysaccharide of the red microalga *Porphyridium* sp." *Journal of Applied Phycology*. vol. 17, 2005, pp. 215-222.

Wen. "Intra-articular Hyaluronic Acid Injections for Knee Osteoarthritis." *American Family Physician*. vol. 62, No. 3, Aug. 1, 2000, pp. 565-570.

Yoshimi et al. "Effects of High-Molecular-Weight Sodium Hyaluronate on Experimental osteoarthrosis Induced by the Resection of Rabbit Anterior Cruciate Ligament." *Clinical Orthopaedics and Related Research*. No. 298, 1994, pp. 296-304.

\* cited by examiner

VISCOSUPPLEMENTATION WITH ALGAL POLYSACCHARIDES IN THE TREATMENT OF ARTHRITIS

FIELD OF THE INVENTION

The present invention relates to compositions comprising algal polysaccharides for use as a viscosupplement in treating joints afflicted with arthritis or with diseases related to joint lubrication.

BACKGROUND OF THE INVENTION

Arthritis is chronic inflammation of the joint, accompanied by pain, swelling and limitation of movement in joints and connective tissue. It afflicts more than 40 million people in the United States. The most prevalent forms of arthritis are osteoarthritis and rheumatoid arthritis, both of them being progressive, degenerative diseases leading to varying degrees of disability. The cartilage and bone of the joint undergo destruction with the progress of the disease, followed by loss of mobility, and increased suffering caused, among others, by the rubbing of bone against bone.

The therapies, available at present, include palliative treatment, based on the use of analgesic or anti-inflammatory agents, and surgical therapy, comprising a partial or total joint replacement. The total replacement is used routinely for the knee, which is the most important joint usually afflicted by the disease. This is an expensive procedure that includes patient discomfort, possible serious post-operative morbidity, and risks associated with surgery involving opening up the joint. The replacement has also a drawback of limited durability, since the implanted prostheses last about 10-15 years. An alternative approach is viscosupplementation which is an injection into the joint of a biocompatible lubricant that reduces friction and pain. The rationale for this approach has its origin in the physiology of joints, where the synovium produces a highly viscous lubricating fluid, consisting of high-molecular-weight substances, such as hyaluronan and lubricin. The highly viscous nature of the synovial fluid is important for normal joint function, since it provides a nearly frictionless interface for joint movement. A molecule of hyaluronan polysaccharide ($3-5\times10^6$ daltons), consisting of monosaccharides N-acetyl glucosamine and glucuronic acid, binds many water molecules in its polyanionic structure, which is important for its mechanical properties. Several viscosupplementation products, based on hyaluronan preparations, have become available in the past few years, aiming to restore the composition of the affected synovial fluid in patients with osteoarthritis, thereby providing these patients with relief from their symptoms. Hyaluronan for these viscosupplements has been usually produced from chicken combs (Synvisc™) or synthetically (Arthrease™).

Several studies have been conducted to evaluate the efficacy of exogenous hyaluronan in the treatment of osteoarthritis, and conflicting results have been reported. In a trial of 91 patients, viscosupplementation of hyaluronan did not have a significantly better effect than placebo in the treatment of osteoarthritis [Henderson K., et al.: Ann. Rheum. Dis. 53 (1994) 529-34]. In another trial, a subgroup of patients older than 60 years with more severe symptoms did report beneficial effects from viscosupplementation therapy [Wen D. Y.: Am. Fam. Physician 62 (2000) 565-70]. A meta-analysis compiling the findings of eight different studies in a total of 971 patients indicated that hyaluronan treatment was superior to a placebo in alleviating osteoarthritis-related symptoms [George E.: Ann. Rheum. Dis. 57 (1998) 637-40]. Limitations of the beneficial effects of hyaluronan injection may result from the limited stability of hyaluronan in synovial fluid. For example, the half-life of hyaluronate in sheep joint was reported to be less than 24 hours [Fraser J. R. E., et al.: Semin. Arthritis Rheum. 22(6S) (1993) 9-17]. Hyaluronic acid is probably hydrolyzed by hyaluronidase enzymes, present in mammalian tissues. Another drawback of viscosupplements made of chicken combs is a possible allergic reaction induced in individuals allergic to avian proteins, feathers, and eggs.

The availability of an efficient viscosupplementation therapy would provide relief to patients afflicted by disorders related to degenerative joint disease with joint lubrication, and in more serious cases, it would postpone the need for surgical intervention and reduce the number of operations performed. It is therefore an object of this invention to provide a viscosupplement composition exhibiting high stability in the synovial fluid.

The polysaccharides of various species of red microalgae were found to be very stable in solution, even when exposed to a wide range of pH values and temperatures [Geresh S., et al.: Biores. Technol. 38 (1991) 195-201]. There are no commercially available enzymes—carbohydrolases—capable of cleaving red microalgal polysaccharides. The main monosaccharides are xylose, glucose and galactose [Gersesh S., et al.: Carbohyd. Res. 208 (1990) 301-5] sulfated at the position 3 or 6 of the monosaccharides glucose and galactose [Lupescu N., et al.: Carbohyd. Res. 210 (1991) 349-52]. The molecular mass of the polysaccharides of the red microalgae has been estimated to be more than 3-5 million daltons.

It is an object of this invention to provide a viscosupplement composition exhibiting high stability in the synovial fluid, containing polysaccharides from red algae.

It is further an object of this invention to provide a viscosupplement composition exhibiting in vitro resistance to hyaluronidase.

Other objects and advantages of present invention will appear as description proceeds.

SUMMARY OF THE INVENTION

This invention provides a composition material containing an algal polysaccharide for use as a viscosupplement, wherein said algal polysaccharide is preferably in an aqueous solution in a concentration of 0.5 to 2% w/w. The composition of the invention has viscosity in the range of 500 to 8,000 cP at room temperature, and is resistant to hyaluronidase (in vitro). Preferred polysaccharides are prepared from algae of genus *Porphyridium*, however other red microalgae may be used. The composition according to the invention may further comprise analgesic agent, anti-inflammatory agent, antimicrobial agent, antiviral agent, anesthetic, muscle relaxant, salts, buffers, diluents, or a medicament needed for treating a concurrent disorder, such as antibiotic, corticoid, antiallergic, or antineoplastic.

This invention further provides use of an algal polysaccharide in treatment of arthritis and other disorders related to joint lubrication, preferably osteoarthritis, rheumatoid arthritis, gout, trauma, (age related) degeneration, said treatment comprising injecting said composition into a joint, which is chosen from knee, hip, shoulder, ankle, elbow, spinal facet joint, or knuckle. The use of an algal polysaccharide in the preparation of a viscosupplement composition for treating arthritis or other disorders related to joint lubrication is also provided.

This invention also relates to a kit comprising sterile equipment for injecting fluids into a joint, a viscosupplement composition comprising an algal polysaccharide, and supplier's instructions.

DETAILED DESCRIPTION OF THE INVENTION

It has now been found that compositions containing polysaccharides of red microalgae belonging to the genera *Porphyridium* are stable in the mammalian synovial fluid, and exhibit superior properties as viscosupplements in the joints. Preliminary results have shown that rabbits knees treated with the polysaccharide showed less degenerative changes in the cartilage when compared with rabbits knees treated with available commercial means.

A solution of algal polysaccharide was separated from *Porphyridium* sp. culture by removing the cells by centrifugation, and then was treated for removal of salts. In concentrations of 0.5% to 2% w/w, water solution of the product had typically viscosity between 500 to 8,000 cP. Liquid compositions were prepared by concentrating the algal polysaccharide from cultures to 0.5-2% in saline solution. The polysaccharide was tested for toxicity and was found to be safe for use on animals (Harlan Biotech Israel). To compare the effects of a composition of this invention and a composition of the prior art, a composition containing either algal polysaccharide or hyaluronan were lo injected to the knees of 6 rabbits, in which experimental osteoarthritis had been induced (12 joints in total), thus 6 joints for each composition, and the effects were examined in the dissected joints after sacrificing the animals at 12 weeks post-operatively. The degenerative changes were less marked in all the animals that had received the algal polysaccharide.

The validation of the results obtained with the pilot study has been initiated with a follow up study on sheep. Briefly, experimental osteoarthritis was induced by lateral menisectomy in both stifle joins of 24 female sheep of same age and stock. After the operation the sheep were free to ambulate for 16 weeks in order to develop osteoarthritis. After 16 weeks the animals were divided into three groups and each group received a treatment regimen including the polysaccharide composition in one knee and a commercial available hyluronan product—Arthrease—in the opposite knee, which will serve as the control group as shown in Table 1.

TABLE 1

Study protocol

| Group number | Right knee | Left knee |
|---|---|---|
| 1 (8 animals) | Polysaccharide single injection | Saline |
| 2 (7 animals) | Polysaccharide single injection | Arthrease single injection once a week for three weeks |
| 3 (7 animals) | Polysaccharide single injection once a week for three weeks | Arthrease single injection once a week for three weeks |

After 12 additional weeks the sheep were sacrificed and the knees dissected. The knees were subjected to histopathological examination and the efficacy of the polysaccharide was established.

The algal polysaccharide of *Porphyridium* in physiological solution and autoclaved, was not degraded by hyluronidase in vitro, as indicated by viscosity measurements.

Thus, without being committed to any theory, it is suggested, and it is a part of this invention, that hyaluronan as a natural lubricating polysaccharide, or as a viscosupplement, can be replaced by another polysaccharide as far as this substitute polysaccharide is polyanionic, high-molecular-weight, non-toxic, and resistant to a hyaluronidase. The anions in said polyanionic polysaccharides can be provided by glucuronic acid, or by ester sulfate groups. Polysaccharides from red microalgae belonging to the genera *Porphyridium* was found by the inventors to be suitable viscosupplements, and the polysaccharide from *Porphyridium* is presented here as a preferred embodiment of this invention. However, other red microalgal genera produce structural polysaccharides that are also useful as components for viscosupplement solutions according to this invention.

This invention provides a composition containing an algal polysaccharide for use as a viscosupplement. A composition of this invention is preferably an aqueous solution, containing an algal polysaccharide in a concentration of from 0.5 to 2% w/w, and has viscosity in the range from 500 to 8000 cP at room temperature. In a preferred embodiment, the composition of this invention comprises a polysaccharide from alga of genus *Porphyridium*, which is dissolved in a saline solution, and has a concentration from 0.5 to 2% w/w, and a viscosity of from 500 to 8,000 cP, preferably at room temperature, and is resistant to hyaluronidase in vitro.

This invention also relates to the use of algal polysaccharides in the preparation of compositions for treating arthritis and other joint disorders, preferably osteoarthritis, rheumatoid arthritis, gout, arthritis, trauma, (age related) degeneration, wherein said composition is preferably a non-immunogenic, non-toxic, water solution having a concentration of said polysaccharide from 0.5 to 2% w/w, and said joints are any one of knee, hip joint, shoulder, ankle, elbow, spinal facet joint, or knuckle.

Compositions according to this invention may comprise an analgesic agent, anti-inflammatory agent, antimicrobial agent, antiviral agent, muscle relaxant, salts, buffers, or diluents. Said composition may further contain a medicament needed for treating a concurrent disorder, said medicament being for example antibiotic, antimycotic, corticoid, anti-allergic, etc.

In a preferred embodiment of this invention, the viscosupplement composition is injected to an afflicted joint, for example in volumes of from about 0.1 to about 5 ml. The algal polysaccharide may be supplied to the afflicted joint in a larger volume of less concentrated solution, or in a smaller volume of more concentrated solution. Water is removed from the joint more quickly than the polysaccharide, and this fact can be taken into consideration, when planning the regimen. In case of a more viscous preparation, a dilution by saline and injecting larger volume can be considered. When determining the size of the injected volume, the size of the treated joint is one of the factors to be considered, and volumes of synovial fluid, known to a skilled person, may be also taken into account. The viscosupplement can be supplied in one portion or repeatedly. In one embodiment, synovial fluid from a knee inflicted by arthritis is removed by a sterile syringe, and 1 ml of 2% solution of the polysaccharide of *Porphyridium* sp. in saline is injected into this knee, this treatment being optionally repeated.

The red algal polysaccharides were found to have anti-inflammatory, anti-oxidant [Matsui S. M. et al.: Biochem. Biotechnol. 104 (2003) 13-22; Tannin-Spitz T. et al.: J. Appl. Phycol. 17 (2005) 215-22], and emollient activities, and the polysaccharide of *Porphyridium* sp. was found, in addition to it, to inhibit Herpes simplex viruses types 1 and 2 and Varicella zoster virus in vitro, with no cytotoxic effects [Arad S. et al.: Recent Advances in Marine Biotechnology: Biomaterials from Aquatic and Terrestrial Organisms. (2005) (In Press)]. These properties may further enhance beneficial properties of algal polysaccharides in their use as viscosupplements in treating joint disorders. This invention provides also use of algal polysaccharides in the treatment of a joint disorder chosen from osteoarthritis, rheumatoid arthritis, gout, trauma, (age related) degeneration, or tumor, comprising i) preparing a composition containing an algal polysaccharide resistant to hyaluronidase; and ii) injecting said composition into an afflicted joint, for example in a volume of from about 0.1 to about 3 ml, either in one portion or repeatedly. Said joint is chosen from knee, hip, shoulder, ankle, elbow, spinal facet joint, or knuckle. Said composition contains an algal polysaccharide in an aqueous solution in a concentration of from about 0.5 to about 2% w/w, and has viscosity in the range of about 500 to about 8,000 cP at room temperature. The polysaccharide is resistant to hyaluronidase in vitro, and is preferably isolated from an alga of genus *Porphyridium*. In some embodiments of the use of algal polysaccharides in the treatment of joint disorders according to this invention, concurrent use of a component chosen from analgesic agent, anti-inflammatory agent, antimicrobial agent, antiviral agent, anesthetic, muscle relaxant, salts, buffers, or diluents is involved. In other embodiments, a medicament needed for treating a concurrent disorder is used, said medicament being chosen from antibiotic, antimycotic, corticoid, antiallergic, or antineoplastic. Said composition is essentially non-immunogenic and non-toxic.

This invention also relates to a kit comprising a sterile equipment for injecting fluids into joints, a viscosupplement composition according to this invention, and supplier's instructions.

The invention will be further described and illustrated in the following non-limiting examples.

EXAMPLES

Cultivation of Algae

*Porphyridium* sp. (UTEX 637) was grown in an artificial sea water (ASW) medium under controlled conditions, and in a large-scale setup, as follows. A piece of slant was transferred aseptically to each sterile Erlenmeyer flask containing 100 ml of ASW. The Erlenmeyer flasks were maintained in a controlled growth room on shaker with light supplied from above by fluorescent lighting of about 90 $\mu Em^{-2}s^{-1}$ intensity, at a temperature of 25±3° C. After 7-10 days, the volume of each Erlenmeyer flask was transferred to a glass column. The columns were maintained under light supplied from the side at an intensity of 150 $\mu Em^{-2}s^{-1}$. The cultures were mixed with air containing 1-3% $CO_2$ at a flow rate of 2 liters per minute. After 3-6 days when the culture had reached 20-50× $10^6$ cells/ml, the entire volume of each column was transferred to a polyethylene sleeve. Each sleeve was filled to a final volume of 3.0 liters of culture containing 5-8×$10^6$ cells/ml. The sleeves were maintained under light supplied from the side at an intensity of 150 $\mu Em^{-2}s^{-1}$. The cultures were mixed with air containing 1-3% $CO_2$ at a flow rate of 2 liters per minute. The logarithmic phase of growth was followed by the stationary phase during which the polysaccharide accumulated in the growth medium. After 15-20 days, the polysaccharide was harvested from the enriched medium.

Isolation of the Algal Polysaccharide

The cells of the red microalgae are encapsulated within a sulfated polysaccharide, the external part of which dissolves in the medium. When the algae are grown in a liquid medium, the viscosity of the medium increases due to the dissolution of the polysaccharide from the cell surface. The entire volume of the culture in the sleeves, as obtained above, was transferred to a large vessel. The cells were separated from the supernatant using a continuous centrifugation (Cepa Z-41 20,000 rpm), and the supernatant was collected. The polysaccharide is treated further by using cross flow filtration technology for removing salts and concentrating the polysaccharide. The final product had >0.9%, viscosity >1400 cP.

Properties of the Algal Polysaccharide

The concentration of the polysaccharides was determined by taking a sample of 0.5 ml of polysaccharide solution with 9.5 ml water. Typical preparation had 0.9%-1% w/w polysaccharide with phenol sulfuric acid according to Dubois M. et al. [Anal. Chem. 28 (1956) 341-354].

Viscosity was measured using Brookfield Digital Viscometer, model DV-II. Sample of 10 ml polysaccharide was measured in spindle no. 25, speed of 30 rpm, and at room temperature.

The polysaccharide has been tested for toxicity (irritation of the eyes) and was found to be safe for use on animals (Harlan Biotech Israel).

Animal Model

An anterior cruciate ligament (ACL) resection animal model for the induction of experimental osteoarthritis in rabbits was used. Briefly, after anesthetization and preparation of two knees, the skin was incised longitudinally for approximately 3 cm medial to the patellar tendon. After opening the joint capsule, the ACL was resected macroscopically. Instability was confirmed manually by performing the anterior drawer sign test. The joint space was flushed with saline and closed with sutures. The animals received post-operative analgesics.

Example 1

Algal polysaccharide and a commercially available hyaluronan were used as viscosupplement in rabbit model. Algal polysaccharide 1% w/w in saline solution, pH 6.5-7.5 was prepared as described above, hyaluronan was obtained 1% w/w, both preparations were sterile. Six rabbits were treated as described above. Beginning one week after the resection ACL, intra-articular injections were given once a week for three consecutive weeks as follows: one knee was injected with hyaluronan preparation (0.1 cc), while the other knee was injected with algal polysaccharide (0.1 cc). Three rabbits were sacrificed at 6 weeks, the remaining animals were sacrificed after 12 weeks. The knee joints were dissected and subjected to histopathological examination according to the modified Mankin criteria [Clinical Orthopedic Research 298 (1994) 296-304]. The degenerative changes were more marked in the knees treated with the control material.

Example 2

The study population comprised 22 healthy female Awassi sheep aged two years. Osteoarthritis was induced by performing a lateral menisectomy under general anesthesia in both stifle joints of each animal. The sheep were allowed to roam free during the first 16 weeks after the surgery, with free access to food and water. By 16 weeks, all the animals walked with a limp. At 16 weeks, the sheep were given intraarticular injections of a microalgal polysaccharide or Arthrease according to the following protocol:

TABLE 2

Study protocol

| Group number | Right knee | Left knee |
|---|---|---|
| 1 (8 animals) | Polysaccharide single injection | Saline |
| 2 (7 animals) | Polysaccharide single injection | Arthrease single injection once a week for three weeks |
| 3 (7 animals) | Polysaccharide single injection once a week for three weeks | Arthrease single injection once a week for three weeks |

For the injections, each joint was accessed by a median approach. The procedure was performed under general anesthesia in an operating room. Following the injections, the sheep were returned to the farm until the end of the study, which lasted for a total of 36 weeks. At the end of that time, the animals were killed, and their knees were dissected. Upon dissection, the knees were assessed by a cartilage-damage grading system, which grades articular cartilage from 0 (normal cartilage), through various stages of damage to 5 (loss of cartilage and exposed bone). After dissection and gross evaluation of the knees, the joint surfaces were decalcified, and two slides were prepared from each joint surface. The slides were stained with hematoxylin & eosin and graded according to an adapted Mankin score, which evaluates cartilage damage.

Results—Macroscopic Evaluation

Matched analysis was performed on each group separately, comparing the right stifle joint to the left. Gross observation showed that the overall score was better for the knees treated with polysaccharide in groups 2 and 3 than in the matched knees treated with three injections of Arthrease, but there were no statistically significant differences among the groups. To evaluate the influence of the polysaccharide and Arthrease on the less severely damaged joints, the evaluation was repeated, with matched analysis, excluding the specimens graded as grades 4 and 5. Again, no statistically significant differences were found among the groups. Unmatched analysis compared a single injection or three injections of polysaccharide with the subgroup of animals receiving three Arthrease injections (groups 2 and 3). Gross observation showed that the overall score for joints treated with three injections of Arthrease (groups 2 and 3) was higher (i.e., worse) than that for the joints treated with polysaccharide injections (groups 2 and 3), Again, no statistically significant differences were was found.

Results—Microscopic Evaluation

Matched analysis was performed on each group separately, in which the right stifle joint was compared to the left. The overall score was better for the knees treated with polysaccharide in group 2 compared with the matched knees treated with three injections of Arthrease. Groups 1 and 3 showed slightly better averages in the left stifle joints than the right stifle joints, which had been treated with polysaccharide. No statistically significant differences were found among the groups. Unmatched analysis compared joints treated with a single injection of polysaccharide with those treated with three injections of Arthrease (groups 1 and 2 right vs. groups 2 and 3 left). The overall score for the knees treated with polysaccharide was lower (i.e., better) than for the knees treated with Arthrease, although no statistically significant differences were found. To evaluate the influence of the polysaccharide and Arthrease on less severely damaged joints, the evaluation was repeated with the exclusion of the specimens graded as grades 4 and 5. Unmatched analysis showed that the overall score for the knees treated with polysaccharide was lower (i.e., better) than for knees treated with Arthrease, although no statistically significant differences were found.

Example 3

The *Porphyridium* sp polysaccharide was resistant toward hyaluronidase in vitro. 1 ml of 0.02% wt % substrate (either hyaluronic acid or algal polysaccharide) in 0.1M phosphate buffer containing 0.15M sodium chloride, pH 5.45, was placed into Oswald viscometer, in bath thermostat at 37° C. After 5 min of incubation, the mammalian hyluronidase (Sigma, H-4272) in the same buffer solution (concentration 0.2 mg/ml) was added into the viscometer, and the count of reaction time started. The time of outflow of the reaction mixture from reservoir of viscometer was determined for reaction lo times 4, 8, 15, 20 and 30 min. Whereas the viscosity of hyaluronic acid was continually decreasing, the viscosity of the algal polysaccharide remained essentially unchanged.

While this invention has been described in terms of some specific examples, many modifications and variations are possible. It is therefore understood that within the scope of the appended claims, the invention may be realized otherwise than as specifically described.

The invention claimed is:

1. A method of treating a joint disorder comprising injecting into a joint of a subject in need thereof a viscous lubricating viscosupplement fluid composition consisting of:
   i) a polysaccharide from a red microalga of the genus *Porphyridium* in an aqueous solution, the polysaccharide being resistant to degradation by hyaluronidase in vitro and having a concentration in said solution of from 0.5 to 2% w/w, and a viscosity of from 500 to 8,000 cP at room temperature; and optionally
   ii) a component selected from the group consisting of pharmaceutically acceptable salt, analgesic agent, anti-inflammatory agent, antimicrobial agent, antibiotic, antimycotic, antioxidant agent, anesthetic, muscle relaxant, antiallergic, and antineoplastic;
   wherein said disorder is selected from the group consisting of arthritis, gout, joint trauma, and joint degeneration.

2. The method according to claim 1, wherein said arthritis is osteoarthritis or rheumatoid arthritis.

3. The method according to claim 1, wherein said joint is selected from the group consisting of a knee, hip, shoulder, ankle, elbow, spinal facet joint, and knuckle.

4. The method according to claim 1, wherein said composition is injected in a volume of from 0.3 to 3 ml.

5. The method according to claim 1, wherein said composition is injected either in one dosage or repeatedly.

* * * * *